United States Patent [19]

Metala et al.

[11] Patent Number: 5,140,264
[45] Date of Patent: Aug. 18, 1992

[54] METHOD FOR NON-DESTRUCTIVELY ASSESSING THE CONDITION OF A TURBINE BLADE USING EDDY CURRENT PROBES INSERTED WITHIN COOLING HOLES

[75] Inventors: Michael J. Metala, Murrysville, Pa.; C. Gerard Beck, Delmar, N.Y.

[73] Assignee: Westinghouse Electric Corp., Pittsburgh, Pa.

[21] Appl. No.: 720,038

[22] Filed: Jun. 24, 1991

[51] Int. Cl.$^5$ ............... G01R 33/12; G01N 27/90
[52] U.S. Cl. .................. 324/219; 324/209; 324/227; 324/232
[58] Field of Search .......... 324/202, 209, 219-221, 324/226, 227, 229-234, 236-243; 73/660, 661, 779; 416/61

[56] References Cited

U.S. PATENT DOCUMENTS

| | | | |
|---|---|---|---|
| 3,407,352 | 10/1968 | Smith | 324/230 |
| 4,086,527 | 4/1978 | Cadot | 324/233 |
| 4,095,181 | 6/1978 | Harris et al. | 324/238 |
| 4,194,149 | 3/1980 | Holt et al. | 324/238 X |
| 4,418,315 | 11/1983 | Edwards et al. | 324/202 |
| 4,460,869 | 7/1984 | Buser et al. | 324/227 X |
| 4,528,856 | 7/1985 | Junker et al. | 73/779 |
| 4,578,643 | 3/1986 | Junker et al. | 324/202 |
| 4,746,858 | 5/1988 | Metala et al. | 324/200 |
| 5,028,100 | 7/1991 | Valleau et al. | 324/232 |

FOREIGN PATENT DOCUMENTS 0141653 11/1980 Japan .................. 324/202

Primary Examiner—Gerard R. Strecker

[57] ABSTRACT

The present invention provides a method and apparatus for performing nondestructive material assessment of service exposed combustion turbine blades. According to the invention, the testing is accomplished by inserting eddy current (EC) probes into the blade's cooling holes, and evaluating the eddy current response of the blade. The eddy current probes are preferably coupled together in a differential mode. The measured response is then compared with a previously determined response corresponding with a known material condition. An assessment of the blade is made on the basis of this comparison.

7 Claims, 3 Drawing Sheets

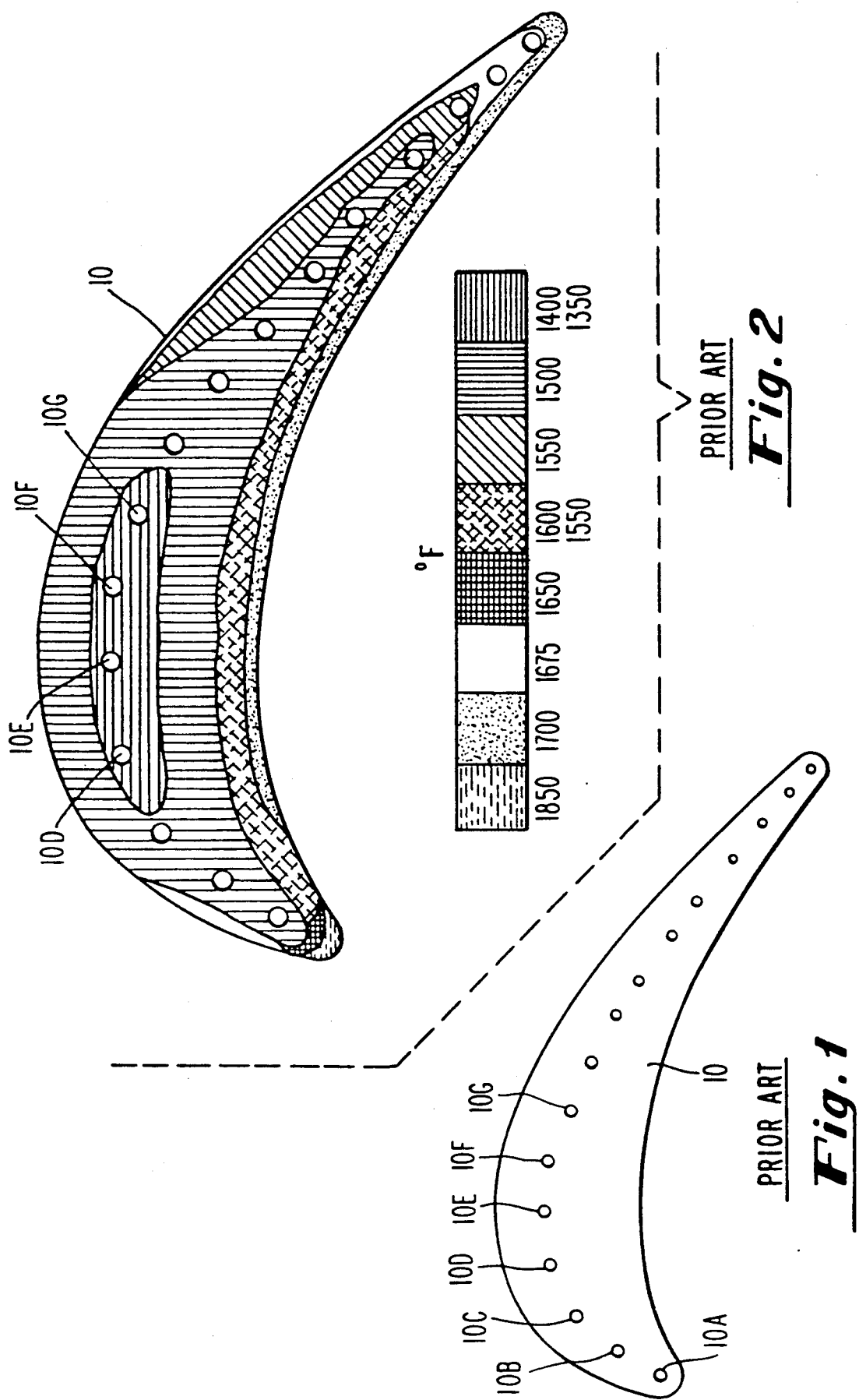

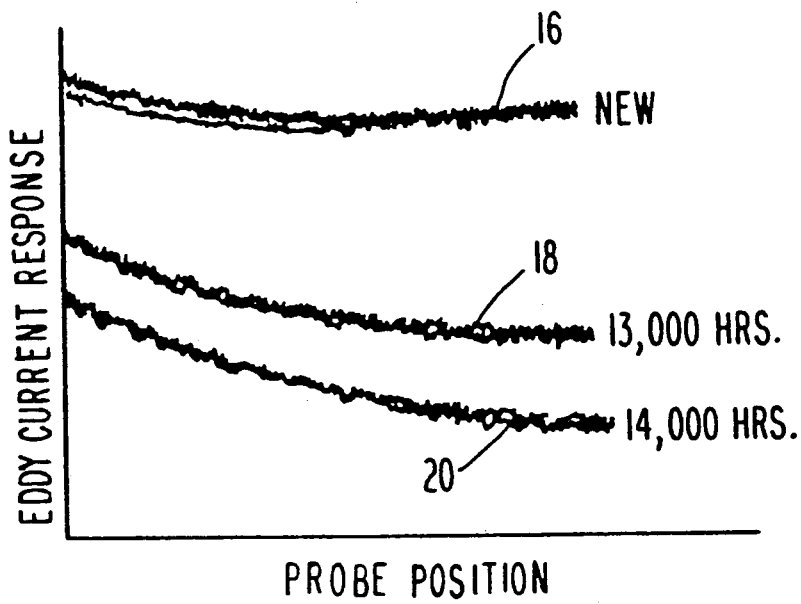
Fig. 3
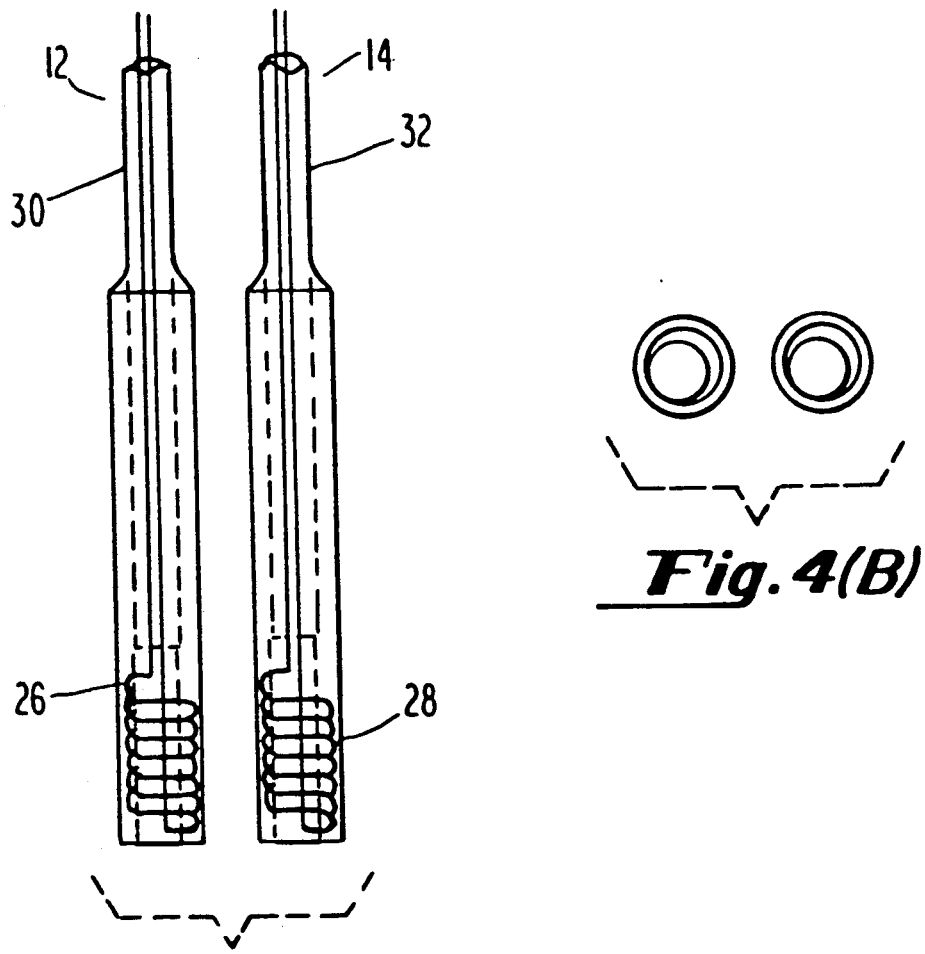
Fig. 4(A)
Fig. 4(B)

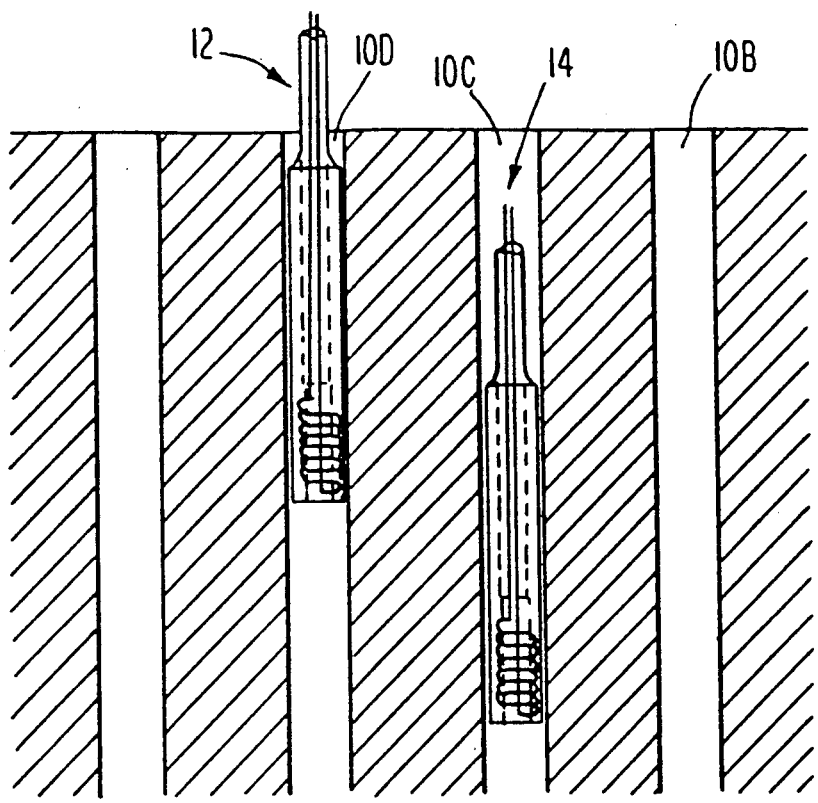
_Fig. 5_
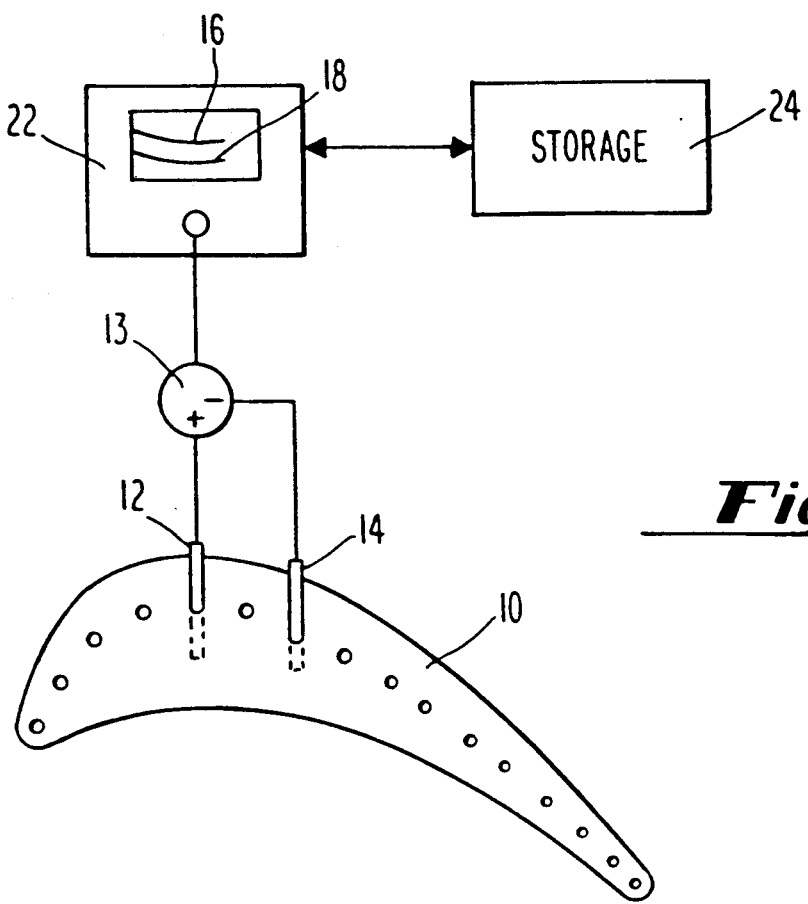
_Fig. 6_

METHOD FOR NON-DESTRUCTIVELY ASSESSING THE CONDITION OF A TURBINE BLADE USING EDDY CURRENT PROBES INSERTED WITHIN COOLING HOLES

BACKGROUND OF THE INVENTION

The present invention relates to methods and apparatuses for the nondestructive assessment of a metallic material. More particularly, the present invention relates to the nondestructive, in situ, material assessment of service-exposed combustion turbine blades.

Metallic components such as industrial gas turbine blades are used under elevated temperature creep conditions and are designed to withstand the maximum stress which can exist in the structure for the required design life. A safety factor is applied to this stress to allow for material variability and variations in the operating conditions. This design stress, if not exceeded, should preclude failure within the design life. In practice, however, the blade experiences considerable mechanical and thermal stresses which can cause damage such as creep (cavitation), microstructural embrittlement and cracking. This damage, if undetected, can result in an unexpected failure, costly repairs and severe damage to the turbine unit.

Periodically, during plant outages, combustion turbine blades that contain no obvious cracks are destructively evaluated in order to monitor and assess the response of blading material to service conditions. During these investigations, stress rupture tests and visual microstructure examinations are performed on selected blades to assess the state of the material and to estimate conditions to which the turbine blades are exposed during service operation. These destructive examinations consist of comparing pre-service and post-service material properties and microstructures. Material specifications serve as a guide in assessing remaining life and the comparison is used to determine whether remaining blades can be put back into service. The advantages of an accurate material assessment method include the avoidance of costly unscheduled outages and the ability to extend the useful life of the blade.

Although analyses of properties from post-service turbine blades provide useful information on life extension, the evaluation process is both time consuming and costly. In addition, the frequent removal of blades for destructive analysis is costly. In the case of combustion turbines, the operation cycle, type of fuel and environmental conditions can vary significantly from machine to machine. For instance, for a given turbine model, some blades may experience higher temperatures than others. As a result, blades can have different microstructures even though they have accumulated the same service exposure time.

Some combustion components operate at very high temperatures (metal temperature between 1500° F. to 1800° F. (815° C. to 982° C.)) and are subjected to different loading ad environmental conditions. FIG. 1 depicts a cross section of a typical combustion turbine blade airfoil 10. Such blades are produced from a high temperature creep resistant non magnetic nickel base superalloy.

The blade comprises a root (not shown) and the airfoil 10. The blade root is used to attach the blade to the turbine disc, and operates at relatively low temperatures, while the airfoil experiences much higher temperatures as it passes through the hot gases created by the combustion process. To keep the airfoil cool during operation, small radial cooling holes 10A, 10B, 10C, etc., are drilled along the length of the airfoil during the manufacturing process. During operation, air passes through these holes, cooling the blade from the interior to the exterior. As a result, large thermal gradients and stresses are created Which can significantly degrade the blade material with time.

When service exposed blades are removed and inspected, significant microstructural and material property differences are observed. These differences can be directly related to the blade's metal temperature and exposure time. In general, service blades which have experienced lower operating temperatures for shorter times have better material properties than those exposed to higher temperatures for longer times.

FIG. 2 depicts the cross-section of a blade's airfoil 10, including a temperature profile from a blade that was in service for 10,000 hours. As shown, the highest metal temperature occurs at the leading and trailing edges and at the concave surface (pressure side) of the blade. Near the centermost cooling holes 10D, 10E, 10F, 10G, lower metal temperatures occur, with the coldest area located in the center of the thick part of the airfoil. The microstructure in the latter area is similar to those of a pre-service blade, i.e., unaffected by service temperature.

Westinghouse Electric Corporation, the assignee of the instant application, has demonstrated that special nondestructive sensors can detect and characterize time-temperature dependent degradation such as creep (U.S. Pat. No. 4,746,858) and temper embrittlement (U.S. Pat. No. 4,528,856) in some materials. These Patents may be referred to for further background on the present invention.

SUMMARY OF THE INVENTION

An object of the present invention is to provide a method and apparatus which, in conjunction with commercially available eddy current instrumentation, can be used to detect, characterize and monitor the extent of time-temperature related damage in metallic materials, such as combustion turbine blades. A further object of the present invention is to eliminate the need for the costly destructive testing typically used to characterize material properties of service exposed turbine blades. A still further object of the present invention is to provide a method and apparatus that can sort the damaged from the undamaged service blades. For sorting by eddy current to be successful, an eddy current "signature" for the blade is preferably acquired immediately after manufacture and periodically during service. (A signature is the measured current through or impedance of an eddy current probe in the vicinity of induced eddy currents, or the difference between the currents through or impedances of two different probes or one probe at two different points along the blade.) For blades already in service, eddy current signatures are not generally available. A second approach is to use a new blade as a reference standard and compare its eddy current response with those from used blades. This may yield erroneous results, however, because manufacturing practices and blades' chemical compositions may have changed over time. This will cause differences in initial properties which may render comparison between old and new blades invalid. The present invention achieves the above objectives by providing a method and apparatus for performing nondestructive material assessment of, e.g., a turbine blade. The method according to the invention employs the detection of eddy current signatures induced in the material being assessed, and correlating the detected signature to a known standard. In addition, the present invention overcomes the aforementioned problems with sorting damaged from undamaged blades through a unique self-calibration scheme.

According to the invention, a pair of eddy current probes are inserted into separate holes in the material (e.g., cooling holes in a turbine blade airfoil). One of the probes is designated the "reference probe," and is inserted into a hole in the thickest region of the blade. This region is apt to be the least affected by heating of the blade. The other probe, designated the "assessment probe," is sequentially inserted into the other cooling holes. At each of the assessment probe positions, an eddy current difference signature (hereinafter eddy current signature) is computed by taking the difference between the current in the assessment probe and the current in the reference probe, e.g., by coupling the two probes to operate in a differential mode. The eddy current signatures are compared with one or more standard signature(s) corresponding to a known condition(s) of the blade material. For example, a standard signature is preferably obtained from the thickest region of the blade, where heating effects are minimal. An estimation of the material condition at each of the assessment probe locations is then made by manually or automatically correlating the measured signatures with one or more signatures corresponding to known conditions of the material.

In its broadest sense, the invention encompasses apparatuses comprising first means for inducing an eddy current in a first region of the material and for detecting a first eddy current signature within the vicinity of the first region, second means for inducing an eddy current in a second region of the material and for detecting a second eddy current signature within the vicinity of the second region, and third means for computing the difference between the first and second eddy current signatures.

A more specific apparatus embodying the invention comprises means for detecting an eddy current signature within the vicinity of a first hole, the first hole defining a reference hole; means for detecting an eddy current signature within the vicinity of a second hole, the second hole defining an assessment hole; and means for computing the difference between the eddy current signatures detected in the vicinity of the reference and assessment holes. The condition of the material is determinable by correlating the difference to a known condition of the material. A preferred embodiment of the invention further includes means for measuring an eddy current signature of a material having a known condition, which signature is indicative of the known condition.

BRIEF DESCRIPTION OF THE DRAWINGS

FIG. 1 depicts a cross section of a known turbine blade airfoil.

FIG. 2 depicts a typical temperature profile of the airfoil of FIG. 1.

FIG. 3 depicts exemplary eddy current signatures of service exposed turbine blades.

FIG. 4(A) is a side view of a pair of eddy current probes in accordance with the present invention.

FIG. 4(B) is a cross sectional view of the eddy current probes of FIG. 4(A).

FIG. 5 depicts the placement of the eddy current probes into cooling holes of a turbine blade.

FIG. 6 is a block diagram of a turbine blade assessment system according to the present invention.

DETAILED DESCRIPTION OF THE PREFERRED EMBODIMENTS

The preferred embodiments will now be described with reference to the drawings, wherein like numerals designate like elements.

FIG. 3 depicts eddy current signatures generated from the surfaces of sections of service blades. The uppermost curve in the figure, i.e., curve 16, is an exemplary eddy current signature of a new turbine blade. Curves 18 and 20 represent eddy current signatures of turbine blades with service histories of 13,000 and 14,000 hours, respectively. According to the invention, these signatures are detected with specially designed eddy current probes 12, 14 (shown in FIG. 4) coupled to a current measurement and display device 22 (see FIG. 6). The eddy current signatures enable one to distinguish between blades with no service history and blades with thousands of hours of service exposure. FIG. 3 depicts the eddy current response, e.g., voltage or impedance, as a function of probe position as the probe is moved closer and closer to a prescribed position within a cooling hole. Thus, off the graph to the left of the vertical axis the three curves 16, 18, 20 would converge, since the probe is far from, and thus unaffected by, the blade. The vertical position of the respective curves at the extreme right (adjacent to the legends "NEW", "13,000 HRS. ", "14,000 HRS.") represents the value of the eddy current response when the probe is inside of the cooling hole.)

According to one embodiment of the invention, a set of eddy current coils 12, 14 are inserted into the cooling holes 10A, 10B, 10C, etc. of a service blade airfoil 10. Since the cooling holes have a very small diameter (e.g., typically 0.050–0.090 in. (1.27–2.29 mm)), the invention comprises a unique eddy current probe design (shown in FIGS. 4(A) and 4(B)), which employs small eddy current coils 26, 28. Coil 26 is part of probe 12, hereinafter referred to as the "reference probe." Coil 28 is part of probe 14, hereinafter referred to as the "assessment probe." (The reason for these labels will become apparent from the remaining detailed description.)

Referring now to FIGS. 4(A) and 4(B), eddy current coils 26, 28 are wound on individual air-core shafts 30, 32, forming a pair of bobbin-like probes. The probes 12, 14 are wired differentially via subtractor 13 and connected to commercially available eddy current test equipment 22, as shown in FIG. 6. The reference probe (probe 12) is inserted into a cooling hole located in the thickest portion of the airfoil 10, e.g., one of holes 10D, 10E, 10F or 10G. As discussed above, this region of the blade operates at relatively low temperatures and will have a microstructure similar to when it was manufactured, and therefore serves as a unique reference point. The assessment probe (probe 14) is then inserted into a neighboring cooling hole. The two probes are then excited, which induces eddy currents in the airfoil 10 in the respective vicinities of the reference and assessment probes, and the current through the assessment coil is subtracted from the current through the reference coil, producing a reference signature. The reference signature is recorded and displayed by the eddy current measurement device 22, and optionally stored in storage device 24. The assessment probe 14 is moved to another cooling hole and the eddy current signature measured at this hole is compared to the reference signature. As the thermal damage, if any, moves from the blade surface inward toward the cooling holes, the eddy current signatures will be affected. Therefore, the measured eddy current signature, corresponding to a given pair of cooling holes in a given blade, can be correlated with a known condition of a similar blade. The correlation may be carried out by visually or automatically comparing measured eddy current signatures with signatures for corresponding holes in a known standard (e.g., an airfoil in a known or reference condition), and interpolating the results to determine the airfoil's condition. The automatic correlation may be carried out by a microprocessor in, e.g., the storage device 24. This procedure is repeated until the eddy current response from all cooling holes 10A, 10B, 10C, etc. has been compared to the signatures of the known standard.

Referring now to FIG. 5, the probes 12, 14 can be positioned to different depths within the cooling holes 10A, 10B, 10C, etc., as shown. This permits an assessment of the blade's degradation from the tip of the blade to the root. In addition, the probes 12, 14 can be pulled or pushed simultaneously along the length of the cooling hole. This allows for automated scanning and computer aided inspection, if so desired. Using computer acquisition and display software, the dynamic scans can be differentially compared and reconstructed to provide a detailed enhanced map of the blade's condition.

In an alternative embodiment of the present invention, the two probes 12, 14 can be connected in a driver/pickup mode. According to this embodiment, the reference probe 12 is pulsed and operated at low frequencies (100 Hz to 10 kHz). The assessment probe 14, is used to receive the electromagnetic signal as it passes through the blade 10.

In a further variation of the invention, the eddy current probes 12, 14 are positioned on the surface of the blade 10. Both the strength of the signal and changes in frequency are monitored and evaluated for changes as a result of material degradation. The principle of the invention, however, remains unchanged. The eddy current probes are employed to detect an eddy current signature, or set of signatures, and these signatures are correlated with a known condition of the material, e.g., corresponding to a known service life and known operating conditions.

It will be apparent to those skilled in the art that many modifications can be made to the above-described preferred embodiments. For example, the invention is not limited to the the specific embodiment of the eddy current probes described above. Accordingly, the scope of the present invention is not intended to be limited by the preferred embodiments, but by the following claims.

We claim:

1. A nondestructive method of assessing the condition of a turbine blade having at least two cooling holes, the method comprising:
   (a) defining at least one of said cooling holes as a reference hole, and at least one other of said cooling holes as an assessment hole;
   (b) inserting a first eddy current probe comprising a first coil into said reference hole, injecting a time-varying current through said first coil so as to induce an eddy current within said turbine blade within the vicinity of said reference hole, and detecting an eddy current response of said first probe;
   (c) inserting a second eddy current probe comprising a second coil into said assessment hole, injecting a time-varying current through said second coil so as to induce an eddy current within said turbine blade within the vicinity of said assessment hole, and detecting an eddy current response of said second probe; and
   (d) assessing the condition of said blade by computing the difference between the respective eddy current responses of the first and second probes, comparing the difference with a predefined response corresponding to a known condition of the blade, and on the basis of the result of the comparison estimating the condition of the blade.

2. A nondestructive turbine blade assessment method as recited in claim 1 further comprising repeating steps (b), (c) and (d) with the eddy current probes inserted to different depths within the reference and assessment holes, thereby providing an assessment of the blade at multiple locations radially along the blade, and estimating on the basis of said assessment the remaining service lifetime of the blade.

3. A nondestructive turbine blade assessment method as recited in claim 1, further comprising: repeating steps (c) and (d) over substantially all of the blade's cooling holes, and thereafter constructing a map of the blade's condition over a cross section of the blade, and estimating on the basis of said map the remaining service lifetime of the blade.

4. A nondestructive turbine blade assessment method as recited in claim 1, wherein steps (a)-(d) are performed with the blade in its operating environment.

5. A nondestructive turbine blade assessment method as recited in claim 1, further comprising the step of, prior to step (b), exposing the turbine blade to a substantially changing magnetic field.

6. A nondestructive turbine blade assessment method as recited in claim 1, wherein the reference holes are defined within an area of the blade where heating effects on the blade are minimal as compared with other areas of the blade.

7. A nondestructive turbine blade assessment method as recited in claim 1, wherein the first and second eddy current probes each comprise an eddy current coil wound around a cylindrical air-core shaft.

* * * * *